(12) United States Patent
Richard et al.

(10) Patent No.: US 8,075,906 B2
(45) Date of Patent: Dec. 13, 2011

(54) MEDICAL DEVICES HAVING POLYMERIC REGIONS WITH COPOLYMERS CONTAINING HYDROCARBON AND HETEROATOM-CONTAINING MONOMERIC SPECIES

(75) Inventors: Robert E. Richard, Wrentham, MA (US); Marlene C. Schwarz, Auburndale, MA (US); Rudolf Faust, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1393 days.

(21) Appl. No.: 11/048,613

(22) Filed: Feb. 1, 2005

(65) Prior Publication Data
US 2006/0171981 A1 Aug. 3, 2006

(51) Int. Cl.
*A61F 2/24* (2006.01)
*A61M 1/12* (2006.01)

(52) U.S. Cl. ..................... 424/423; 604/891.1

(58) Field of Classification Search .................. 424/423; 604/891.1
See application file for complete search history.

(56) References Cited

U.S. PATENT DOCUMENTS

| | | | | |
|---|---|---|---|---|
| 4,182,818 | A | 1/1980 | Tung et al. | 526/173 |
| 5,733,925 | A | 3/1998 | Kunz et al. | 514/449 |
| 5,788,687 | A | 8/1998 | Batich et al. | 604/890.1 |
| 6,545,097 | B2 | 4/2003 | Pinchuk et al. | 525/240 |
| 6,576,310 | B2 * | 6/2003 | Shimada | 428/36.9 |
| 6,818,247 | B1 | 11/2004 | Chen et al. | 427/2.24 |
| 2002/0107330 | A1 | 8/2002 | Pinchuk et al. | 525/242 |
| 2002/0193475 | A1 | 12/2002 | Hossainy et al. | 524/114 |
| 2003/0065355 | A1 | 4/2003 | Weber | 606/200 |
| 2003/0093107 | A1 | 5/2003 | Parsonage et al. | 606/194 |
| 2003/0171496 | A1 | 9/2003 | Pinchuk et al. | 525/242 |
| 2003/0235602 | A1 | 12/2003 | Schwarz | 424/424 |
| 2003/0236513 | A1 * | 12/2003 | Schwarz et al. | 604/890.1 |
| 2003/0236514 | A1 | 12/2003 | Schwarz | 604/890.1 |
| 2004/0024098 | A1 | 2/2004 | Mather et al. | 524/268 |
| 2004/0030062 | A1 | 2/2004 | Mather et al. | 526/72 |
| 2004/0035290 | A1 | 2/2004 | Sammons et al. | 95/45 |
| 2004/0054047 | A1 | 3/2004 | Lai et al. | 524/268 |
| 2004/0092653 | A1 | 5/2004 | Ruberti et al. | 524/563 |
| 2004/0116641 | A1 | 6/2004 | Mather et al. | 528/28 |
| 2004/0148002 | A1 * | 7/2004 | Cheng et al. | 623/1.11 |
| 2004/0170752 | A1 | 9/2004 | Luthra et al. | 427/2.24 |
| 2004/0171740 | A1 | 9/2004 | Ruberti et al. | 524/563 |
| 2005/0010275 | A1 | 1/2005 | Sahatjian et al. | 623/1.11 |
| 2005/0025802 | A1 | 2/2005 | Richard et al. | 424/423 |
| 2005/0025803 | A1 | 2/2005 | Richard et al. | 424/423 |
| 2005/0027283 | A1 | 2/2005 | Richard et al. | 604/890.1 |
| 2005/0064011 | A1 | 3/2005 | Song et al. | 424/423 |
| 2005/0176891 | A1 | 8/2005 | Faust et al. | 525/193 |
| 2005/0187414 | A1 | 8/2005 | Faust et al. | 568/687 |
| 2006/0013854 | A1 | 1/2006 | Strickler et al. | 424/423 |
| 2006/0013867 | A1 | 1/2006 | Richard et al. | 424/449 |

FOREIGN PATENT DOCUMENTS

| | | |
|---|---|---|
| EP | 1 123 715 A2 | 8/2001 |
| EP | 1 440 698 A1 | 7/2004 |
| WO | WO 2005/011766 A1 | 2/2005 |
| WO | WO 2005/069966 A2 | 8/2005 |

OTHER PUBLICATIONS

Jen-Ming Yang, et al., "Radiation-Induced Graft Copolymer SBS-g-VP for Biomaterial Usage", *Journal of Biomedical MaterialsResearch*, 1996, vol. 31, pp. 281-286.
Guido Kickelbick, "Concepts for the Incorporation of Inorganic Building Blocks Into Organic Polymers on Nanoscale", *Progress in Polymer Science*, 28 (2003), pp. 83-114.
Xianyi Cao, et al., " Polyisobutylene-Based Thermoplastic Elastomers. 5 Poly(styrene-b-isobutylene-b-styrene) Triblock Copolymers by Coupling of Living Poly(styrene-b-isobutylene) Diblock Copolymers", *Macromolecules*, 1999, 32(17), p. 5487-5494.
Miklos Györ, et al., "Living Carbocationic Polymerization of Isobutylene with Blocked Bifunctional Initiators in the Presence of DI-tert-Butylpyridine as a Proton Trap", *J. Macromol. Sci.-Pure Appl. Chem.*, (1992), A29 (8), p. 639-653.
Gábor Kaszás, et al., "Quasiliving Carbocationic Polymerization; XII. Forced Ideal Copolymerization of Isobutylene with Styrene", *J. Macromol. Sci.—Chem.*, 1982-83, A18(9), pp. 1367-1382.
R. H. Wiley, et al., "Isolation of Pure p- Divinylbenzene from Commercial Divinylbenzene", *Journal of Polymer Science : Part A-1*, 1968, 6(4), pp. 1065-1066.
Il-Jin Kim, et al., Synthesis and Characterization of Novel Chlorosilyl Functional Polyisobutylene, *Polymer Preprints*, (Am. Chem. Soc. Div. Polym. Chem.), 2000, 41(2), pp. 1309-1310.
Timothy S. Haddad, et al., "Hybrid Organic-Inorganic Thermoplastics: Styryl-Based Polyhedral Oligomeric Silsesquioxane Polymers", *Macromolecules* 1996, 29, pp. 7302-7304.
Akira Hirai, et al., "Polymerization of Monomers Containing Functional Groups Protected by Trialkylsilyl Groups, 1", *Makromol. Chem., Rapid Commun.* 1982, 3, pp. 941-946.
Savvas Hadjikyriacou, et al., Amphiphilic Block Copolymers by Sequential Living Cationic Polymerization: Synthesis and Characterization of Poly(isobutylene-b-methyl vinyl ether), *Macromolecules* 1996, 29, pp. 5261-5267. P. J. Reed, et al., "The Preparation and Analysis of High Purity Organolithium Initiators", *Journal of Organometallic Chemistry*, (39) 1972, pp. 1-10.
William G. Ruth, et al., "Silicon-Mediated Synthesis of New Amphiphilic Oligomers", *Journal of Polymer Science: Part A: Polymer Chemistry*, vol. 35, (1997), pp. 163-170.
Sipos, Laszlo et al., "Controlled Delivery of Paclitaxel from Stent Coatings Using Poly(hydroxystyrene-b-isobutylene-b-hydroxystyrene) and Its Acelylated Derivative," Biomacromolecules 2005, 6, pp. 2570-2582.
Riesen et al., "Die Glasubergangstemperatur gemessen mit verschiedenen TA-Techniken, Teil 2: Ermittlung der Glasubergangstemperaturen," USERCOM Feb. 2003. (in German) (Cited but not relied upon in an Office Action in counterpart EP 06719375.5). A machine translation of the Title and Abstract, in English, is attached.

(Continued)

*Primary Examiner* — Jeffrey S. Lundgren
*Assistant Examiner* — Nelson Blakely, III
(74) *Attorney, Agent, or Firm* — Mayer & Williams PC; David B. Bonham; Keum J. Park (57) ABSTRACT

According to an aspect of the present invention, implantable or insertable medical devices are provided, which contain one or more polymeric regions. These polymeric regions, in turn, contain one or more polymers, at least one of which is a copolymer that includes the following: (a) one or more unsaturated hydrocarbon monomer species and (b) one or more heteroatom-containing monomer species.

8 Claims, 4 Drawing Sheets

OTHER PUBLICATIONS

"Silsesquioxanes", Applications, 4 pages. http://www.sigmaaldrich.com/img/assets/3900/Silsesquioxanes-POSSMonomers.pdf, 2000.

"Hybrid Plastics Superior Technology for Superior Products," Poss Technology, 2 pages. http://www.hybridplastics.com/posstech.html, Dec. 2, 2005.

"Silica-Based Nanocomposites", 3 pages. http://www.azom.com/details.asp?ArticleID=938, Dec. 2 2005.

Kim, Il-Jin et al., "Living Cationic Block Copolymerization of Isobutylene with Styrl-POSS Macromers," Polymer Preprints (American Chemical Society, Division of Polymer Chemistry) (2004), 45(1), pp. 1106-1107.

Sipos, Laszlo et al. "Synthesis of poly(4-hydroxstyrene)-b-isobutylene-b-(4-hydroxystyrene)] triblock copolymers via living Cationic sequential block copolymerization of isobutylene with 4-tert-butyidimethylsilyloxy) styrene." Polymer Preprints (American Chemical Society, Division of Polymer Chemistry), (2004), 45(1), pp. 1101-1102.

Cho, Jae Cheol et al., "Synthesis of poly(isobutylene)-poly(alkyl methacrylate) block copolymers by the combination of cationic and anionic polymerizations," Polymer Preprints (American Chemical Society, Division of Polymer Chemistry) 2004, 45(1), pp. 1099-1100.

Zhou, Y. et al., "Synthesis of poly(isobutylene-b-tert-butyl vinyl ether) and poly(isobutylene-b-tert-butyldimethylsilyl vinyl ether) diblock copolymers." Polymer Preprints (American Chemical Society, Division of Polymer Chemistry) 2003, 44(2), pp. 681-682.

Sipos, L. et al., "Controlled Delivery of Paclitaxtel from Stent Coatings Using Poly(hydroxystyrene-b-isobutylene-b-hydroxystyrene and its Acetylated Derivative." Polymeric Materials: Science and Engineering Preprints, 2005, 92, pp. 41-42.

Cho, J.C. et al., "Synthesis, Characterization, and Drug Release Properties of Poly(methyl methacrylate-b-isobutylene-b-methyl methacrylate) and (hydroxyethyl methacrylate-b-isobutylene-b-hydroxymethyl methacrylate)" Polymer Preprints (American Chemical Society, Division of Polymer Chemistry) 2005, 46(1), pp. 105-106.

Judit E. Puskas et al., "Polyisobutylene-Based Biomaterials", Department of Polymer Science, College of Polymer Science and Polymer Engineering, The University of Akron, 62 pages, 2004.

* cited by examiner

MEDICAL DEVICES HAVING POLYMERIC REGIONS WITH COPOLYMERS CONTAINING HYDROCARBON AND HETEROATOM-CONTAINING MONOMERIC SPECIES

FIELD OF THE INVENTION

The present invention relates generally to medical devices, and more particularly to implantable or insertable medical devices which contain polymeric regions.

BACKGROUND OF THE INVENTION

Materials which are suitable for use in making implantable or insertable medical devices typically exhibit one or more of the qualities of exceptional biocompatibility, extrudability, moldability, fiber forming properties, tensile strength, elasticity, durability, and the like. Moreover, in medical devices from which a therapeutic agent is released, suitable materials for use will typically exhibit a release profile appropriate for the disease or condition being treated.

In this regard, controlled release of therapeutic agents by means of polymeric materials has existed in various forms for many years. For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

Consequently, there is a continuing need for high performance polymeric materials that can be used in medical devices, including those which regulate the release therapeutic agents. Among various attributes of the polymer or polymers making up such materials, the molecular weight, architecture (e.g., linear, cyclic, branched), monomeric constituents, as well as the proportion and distribution of the monomeric constituents (where copolymers are involved) will commonly influence one or more characteristics of the materials, including the biocompatibility, mechanical characteristics, processability, and therapeutic agent release profile (where a therapeutic agent is present and is released).

SUMMARY OF THE INVENTION

According to an aspect of the present invention, implantable or insertable medical devices are provided, which contain one or more polymeric regions. These polymeric regions, in turn, contain one or more polymers, at least one of which is a copolymer that includes: (a) one or more unsaturated hydrocarbon monomer species (wherein a hydrocarbon monomer species is one that contains only hydrogen and carbon atoms, for example, ethylene, propylene, isopropylene, butylene, isobutylene, etc.) and (b) one or more heteroatom-containing monomer species (wherein a heteroatom is an atom other carbon or hydrogen), for example, vinyl amine monomer species such as vinyl pyridine, POSS monomer species, protected and unprotected hydroxystyrene monomer species, vinyl alcohol, and high $T_g$ vinyl ethers.

For example, in some embodiments, the polymeric regions contain one or more polymers, at least one of which is an elastomeric block copolymer that includes: (a) one or more polymer blocks containing one or more unsaturated hydrocarbon monomer species and (b) one or more polymer blocks containing one or more heteroatom-containing monomer species, with the proviso that the polymer block does not contain a heteroatom-containing monomer species selected from maleic anhydride monomer species, methyl methacrylate monomer species, ethyl methacrylate monomer species and hydroxyethyl methacrylate monomer species.

Furthermore, in some embodiments of the invention, the polymeric regions control the release of one or more therapeutic agents, in which case the therapeutic agent is, for example, disposed beneath and/or within the polymeric region.

Advantages of the present invention are that polymeric regions can be formed which have one or more enhanced characteristics selected from the following: tensile strength, modulus, durability, biocompatibility, biostability, processability, and therapeutic agent storage and release (i.e., where a therapeutic agent is present), and so forth.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

All publications, patents and patent applications cited herein, whether supra or infra, are hereby incorporated by reference in their entirety.

As noted above, in one aspect, the present invention provides implantable or insertable medical devices, which contain one or more polymeric regions. These polymeric regions, in turn, contain one or more polymers, at least one of which is a copolymer that includes:

According to an aspect of the present invention, implantable or insertable medical devices are provided, which contain one or more polymeric regions. These polymeric regions, in turn, contain one or more polymers, at least one of which is a copolymer that includes: (a) one or more unsaturated hydrocarbon monomer species and (b) one or more heteroatom-containing monomer species.

For example, in some embodiments, the polymeric regions contain one or more polymers, at least one of which is an elastomeric block copolymer that includes: (a) one or more first polymer blocks containing one or more unsaturated hydrocarbon monomer species and (b) one or more second polymer blocks containing one or more heteroatom-containing monomer species, with the proviso that the polymer block does not contain a heteroatom-containing monomer species selected from maleic anhydride monomer species, methyl methacrylate monomer species, ethyl methacrylate monomer species and hydroxyethyl methacrylate monomer species.

Unsaturated hydrocarbon monomers generally have low polarity due to the fact that hydrogen and carbon have relatively low electronegativities. Heteroatom-containing monomer species are generally more polar that unsaturated hydrocarbon monomer species, because they typically contain atoms (e.g., O, N, S, P) that have electronegativities that are significantly higher than those of hydrogen and carbon. For this reason, the first polymer blocks containing one or more unsaturated hydrocarbon monomer species are generally less polar than the second polymer blocks containing one or more heteroatom-containing monomer species.

Medical devices benefiting from the present invention include a variety of implantable or insertable medical devices, which are implanted or inserted into a subject, either for procedural uses or as implants. Examples include catheters (e.g., renal or vascular catheters such as balloon catheters), guide wires, balloons, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, tissue bulking devices, tissue engineering scaffolds for cartilage, bone, skin and other in vivo tissue regeneration, sutures, suture anchors, anastomosis clips and rings, tissue staples and ligating clips at surgical sites, cannulae, metal wire ligatures, orthopedic prosthesis such as bone grafts, bone plates, joint prostheses, as well as various other medical devices that are adapted for implantation or insertion into the body.

The medical devices of the present invention include implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects. Specific examples of medical devices for use in conjunction with the present invention include vascular stents, such as coronary stents and cerebral stents, which deliver a therapeutic agent into the vasculature for the treatment of restenosis.

In some embodiments, the polymeric regions of the present invention correspond to an entire medical device. In other embodiments, the polymeric regions correspond or to one or more portions of a medical device. For instance, the polymeric regions can be in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes (e.g., in desired patterns, for instance, using appropriate masking techniques, such as lithographic techniques), and they can be formed from a variety of polymeric materials. Materials for use as underlying medical device substrates include ceramic, metallic and polymeric substrates. The substrate material can also be a carbon- or silicon-based material. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

In some aspects, the polymeric regions of the present invention control the release of one or more therapeutic agents, in which case the therapeutic agent is disposed, for example, beneath and/or within the polymeric region. Such "polymeric release regions" include carrier regions and barrier regions. By "carrier region" is meant a polymeric release region which further comprises a therapeutic agent and from which the therapeutic agent is released. For example, in some embodiments, the carrier region constitutes the entirety of the medical device (e.g., provided in the form of a stent body). In other embodiments, the carrier region corresponds to only a portion of the device (e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

In addition to the attributes of the polymer or polymers making up the polymeric release regions, the therapeutic agent release profile is also affected by other factors such as the size, number and/or position of the polymeric release regions within the device. For example, the release profile of polymeric carrier and barrier layers in accordance with the presenting invention can be modified by varying the thickness or surface areas of the same. Moreover, multiple polymeric regions can be employed to modify the release profile. For example, multiple carrier or barrier layers of the invention, either having the same or different content (e.g., different polymeric and/or therapeutic agent content), can be stacked on top of one another (hence, carrier layers can act as barrier layers in some embodiments), can be positioned laterally with respect to one another, and so forth.

As a specific example, for tubular devices such as stents (which can comprise, for example, a laser or mechanically cut tube, one or more braided, woven, or knitted filaments, etc.), polymeric release layers can be provided on the luminal surfaces, on the abluminal surfaces, on the lateral surfaces between the luminal and abluminal surfaces (including the ends), patterned along the luminal or abluminal length of the devices, and so forth. Moreover, release layers can control the release of the same or differing underlying therapeutic agent. It is therefore possible, for example, to release the same or different therapeutic agents at different rates from different locations on the medical device. As another specific example, it is possible to provide a tubular medical device (e.g., a vascular stent) having a first release layer which contains or is disposed over a first biologically active agent (e.g., an antithrombotic agent) at its inner, luminal surface and a second release layer which contains or is disposed over a second biologically active agent that differs from the first biologically active agent (e.g., an antiproliferative agent) at its outer, abluminal surface (as well as on the ends, if desired).

Medical devices having sustained release profiles are beneficial in some embodiments of the invention. By "sustained release profile" is meant a release profile in which more than 50% of the total release from the medical device that occurs over the course of implantation/insertion in the body occurs subsequent to 1 day of administration (or in some embodiments subsequent to 2, 4, 8, 16, 32, 64, 128 or even more days of administration). Conversely, this means that less 50% of the total release from the medical device occurs before the device has been implanted/inserted for the same period.

As noted above, polymeric regions in accordance with the present invention contain one or more polymers, at least one of which is a copolymer that includes the following: (a) one or more unsaturated hydrocarbon monomer species (e.g., ethylene, propylene, butylene, isobutylene, etc.) and (b) one or more heteroatom-containing monomer species (e.g., vinyl amine monomer species such as vinyl pyridine, POSS monomer species, protected and unprotected hydroxystyrene monomer species, vinyl alcohol, high $T_g$ vinyl ethers, etc.).

As used herein a "polymeric region" is a region that contains one or more polymers, typically at least 50 wt % polymer, at least 75 wt % polymer, or even more.

As used herein, "polymers" are molecules that contain one or more chains, each containing multiple copies of the same or differing constitutional units, commonly referred to as monomers. An example of a common polymer chain is polystyrene where n is an integer of 10 or more, more typically on the order of 10's, 100's, 1000's or even more, in which the chain contains styrene monomers:

(i.e., the chain originates from, or has the appearance of originating from, the polymerization of styrene monomers, in this case, the addition polymerization of styrene monomers).

Polymers for use in the polymeric regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others.

The polymers for use in the polymeric regions of the present invention can contain, for example, homopolymer chains, which contain multiple copies of a single constitutional unit, and/or copolymer chains, which contain multiple copies of at least two dissimilar constitutional units, which units may be present in any of a variety of distributions including random, statistical, gradient and periodic (e.g., alternating) distributions.

"Block copolymers" are polymers containing two or more differing homopolymer or copolymer chains. In certain embodiments, for example, the polymeric regions of the present invention are provided with a block copolymer that contains (a) one or more unsaturated hydrocarbon polymer chains containing one or more unsaturated hydrocarbon monomer species (designated below as "U") and (b) one or more additional polymer chains containing one or more heteroatom-containing monomer species, for example, selected from vinyl amine monomer species such as vinyl pyridine monomer species, POSS monomer species, protected and unprotected hydroxystyrene monomer species, vinyl alcohol and high $T_g$ vinyl ethers (designated below as "A").

Examples of such structures include (a) block copolymers having alternating blocks of the type $(AU)_m$, $U(AU)_m$ and $A(UA)_m$ where m is a positive whole number of 1 or more, and (b) star block copolymers having multi-arm geometries such as $X(UA)_n$, and $X(AU)_n$, where n is a positive whole number of 3 or more, and X is a hub species (e.g., an initiator molecule residue, a residue of a molecule to which preformed polymer chains are attached, etc.) In addition to the hub species mentioned above, copolymers such as those above can contain a variety of other non-polymer-chain species, which are commonly present in copolymers, including capping molecules, and linking residues.

Other examples of copolymers include comb copolymers having a U chain backbone and multiple A side chains, as well as comb copolymers having an A chain backbone and multiple U side chains. For the purposes of the present invention, comb copolymers are considered to be a class of copolymers distinct from block copolymers.

By "unsaturated hydrocarbon monomer" is meant a linear or branched monomer consisting of hydrogen and carbon atoms and containing one or more carbon-carbon double bonds which can participate in polymerization. Typically, the unsaturated hydrocarbon monomers for use in conjunction with the present invention contain from 2 to 12 carbon atoms.

Examples of unsaturated hydrocarbon monomers, along with a published glass transition temperature ($T_g$) of the corresponding homopolymer, include the following: ethylene, propylene ($T_g$ -8 to -13° C.), isobutylene ($T_g$ -73° C.), 1-butene ($T_g$ -24° C.), 4-methyl pentene ($T_g$ 29° C.), 1-octene ($T_g$ -63° C.) and other α-olefins, as well as trans-butadiene ($T_g$ -58° C.), cis-isoprene ($T_g$ -63° C.), and trans-isoprene ($T_g$ -66° C.).

Unsaturated hydrocarbon monomers generally have low polarity due to the fact that hydrogen and carbon have relatively low electronegativites. Moreover, unsaturated hydrocarbon monomers are typically "low glass transition temperature (low $T_g$) monomers," by which is meant that, when polymerized, they form homopolymers displaying having a $T_g$ that is below ambient temperature, more typically below about 20° C., below about 0° C., below about -25° C., or even below about -50° C. "Ambient temperature" is 25° C.-45° C., more typically body temperature (e.g., 35° C.-40° C.). Conversely, elevated or "high $T_g$ monomers" are those that, when polymerized, form homopolymers displaying a glass transition temperature that is above ambient temperature, more typically above 50° C., above 75° C. or even above 100° C. $T_g$ can be measured by any of a number of techniques including differential scanning calorimetry (DSC), dynamic mechanical analysis (DMA), or dielectric analysis (DEA). Polymer chains formed from low $T_g$ monomers are typically soft and elastomeric at ambient temperature, whereas polymer chains formed from high $T_g$ monomers are hard at ambient temperature.

Polymeric regions containing copolymers that have both low and high $T_g$ polymer chains (e.g., diblock copolymers having low and high $T_g$ chains, triblock copolymers having a low $T_g$ central chain or "midblock" and one or more high $T_g$ end chains or "endblocks", triblock copolymers having a high $T_g$ midblock and one or more low $T_g$ endblocks, comb copolymers having a low $T_g$ main chain and multiple high $T_g$ side chains, comb copolymers having a high $T_g$ main chain and multiple low $T_g$ side chains, and so forth) commonly contain distinct low and high $T_g$ polymer phases, which provide these regions with various interesting properties.

As a specific example, block copolymers of polyisobutylene and polystyrene, for example, polystyrene-polyisobutylene-polystyrene triblock copolymers (SIBS copolymers), described in U.S. Pat. No. 6,545,097 to Pinchuk et al., which is hereby incorporated by reference in its entirety, have proven valuable as release polymers in implantable or insertable drug-releasing medical devices. These copolymers are particularly useful for medical device applications because of their excellent strength, biostability and biocompatibility, particularly within the vasculature. For example, these copolymers exhibit high tensile strength, which frequently ranges from 2,000 to 4,000 psi or more, and resist cracking and other forms of degradation under typical in vivo conditions.

As noted above, in addition to one or more unsaturated hydrocarbon monomer species, copolymers used in conjunction with the present invention also contain one or more heteroatom-containing monomer species. Such monomers are generally more polar that unsaturated hydrocarbon monomers, because they typically contain atoms (e.g., O, N, S, P) that have electronegativities that are higher than those of hydrogen and carbon atoms. Examples of heteroatom-containing monomer species include, for example, vinyl amine monomer species such as vinyl pyridine monomer species, POSS monomer species, protected and unprotected hydroxystyrene monomer species, vinyl alcohol, high $T_g$ vinyl ethers, and so forth.

Examples of vinyl pyridine monomer species, along with a published $T_g$ of the corresponding homopolymer, include 2-vinyl pyridine ($T_g$ 104° C.), 3-vinyl pyridine, 4-vinyl pyridine ($T_g$ 142° C.). Examples of copolymers for use in the present invention include those containing 50 to 90 wt % unsaturated hydrocarbon monomer species and 10 to 50 wt % vinyl pyridine monomer species.

When vinyl pyridine monomer species are copolymerized with low $T_g$ monomers (such as the above unsaturated hydrocarbon monomer species) or where they are otherwise included within copolymers containing low $T_g$ monomers (e.g., where the copolymer contains one or more polymer chains that contain vinyl pyridine monomer species and one or more chains that contain low $T_g$ monomers), then the high glass transition temperature characteristics of the vinyl pyridine species within the resulting copolymers tends to increase the hardness of the resulting copolymers (and thus polymeric regions containing the resulting copolymers). Moreover, the high glass transition temperature characteristics of the vinyl pyridine species within the resulting copolymers may also tend to decrease the tack of the resulting copolymers, and thus that of polymeric regions containing the resulting copolymers (e.g., in instances where polyisobutylene is present in the polymeric region). Furthermore, compared to unsaturated hydrocarbon monomer species (as well as many other monomer species) vinyl pyridines are relatively polar/hydrophilic. Hence the presence of vinyl pyridine species within the resulting copolymers will increase the overall polarity/hydrophilicity of the resulting copolymers (and thus polymeric regions containing the resulting copolymers). This increase in polarity/hydrophilicity will affect various properties of the polymeric regions, including water uptake/swelling, drug diffusion and release (thereby affecting the release profile, etc.), polymer/therapeutic interactions, and biocompatibility.

Silsesquioxanes are a class of compounds with the empirical formula $RSiO_{1.5}$. These compounds derive their name from the one-and-one-half (1.5) or "sesqui"-stoichiometry of the silica and oxygen atoms in the core structure. Several structural representations of silsesquioxanes with the empirical formula $RSiO_{1.5}$ are possible, with the two of the more common representations being those with ladder-type core structures such as and with cage-like core structure, such as the following, which contains eight silicon atoms:

This structure is commonly called a T8 "cube," but if the bonds are drawn at their true angles the actual structure is not a true cube. However, the cubic structure is easy to depict and visualize and is thus commonly used to represent the structure.

Each R group can independently be a relatively inert species, such as hydrogen, or an organic radical such as alkyl, cycloalkyl, aryl, alkyl-aryl, or alkoxy radical, for example, having from 1-12 carbon atoms. (Many silsesquioxanes have significant solubility in common organic solvents such as chloroform, hexane and tetrahydrofuran due to the presence of hydrophobic R groups.)

One or more of the R groups within the silsesquioxanes can also correspond to reactive/polymerizable entities such as acrylics, methacrylics, α-olefins, vinyl groups, other species containing unsaturation (e.g., norbornenyl), epoxies, carboxylic acids, esters, halides, organohalides, isocyanates, amines, alcohols, silanes, silanols, siloxanes, and so forth, which can be can be either copolymerized with a range of monomers, or grafted onto polymer chains. Such silsesquioxanes are sometimes called Polyhedral Oligomeric SilSesquioxanes (POSS) monomers. Copolymers containing POSS monomers can be thought of as organic-inorganic nanocomposites.

Copolymers for use in the present invention include those containing 50 to 90 wt % unsaturated hydrocarbon monomer species and 10 to 50 wt % POSS monomers.

Numerous POSS monomers are available or can be readily synthesized, several of which are listed in U.S. Patent Application Publication 2004/0035290, which as noted above, is incorporated by reference. Examples include various 1-[substituted]-3,5,7,9,11,13,15-heptacyclopentylpentacyclo[9.5.1.13,9.15,15.17,13]-octasiloxanes, including those with the following substitutions: 1-[3-(allylbisphenol A)propyldimethylsiloxy]-, 1-[3-(allylbiphenol)propyldimethylsiloxy]-, 1-[3-(1,3-propanediol-2-ethyl-2-methyloxy)propyldimethylsiloxy]-, 1-[(2-methyl,2-hydroxy)butyldimethylsiloxy]-, 1-[3-(ethoxydimethylsilyl)propyl]-, 1-[2-(diethoxymethylsilyl)propyl]-, 1-[3-(triethoxysilyl)propyl]-, 1-[2-(ethoxydimethylsilyl)ethyl]-, 1-[2-(diethoxymethylsilyl)propyl]-, 1-[2-(triethoxysilyl)propyl]-, 1-chloro-, 1-[2-(chlorodimethylsilyl)ethyl]-, 1-[2-(dichloromethylsilyl)ethyl]-, 1-[2-(trichlorosilyl)ethyl], 1-[3-(chlorodimethylsilyl)propyl]-, 1-[3-(dichloromethylsilyl)propyl]-, 1-[3-(trichlorosilyl)propyl]-, 1-[(2-epoxy)propyl]-, 1-[2-(cyclohexyl-3-epoxy)ethyl]-, 1-[methylpropionato]-, 1-[ethylundecanoato]-, 1-[(3-chloro)propyl]-, 1-[4-chlorophenyl]-, 1-[chlorobenzyl]-, 1-[2-(chlorobenzyl)ethyl]-, 1-[3-(methacryl)propyl]-, 1-[3-(methacryl)propyldimethylsiloxy]-, 1-[(3-cyano)propyl]-, 1-[2-(norbornen-2-yl)ethyl]-, 1-[2-(norbornen-2-yl)ethyldimethylsiloxy]-, 1-[3-(allylbisphenol A)propyldimethylsiloxy]-, 1-[3-(allylbiphenol)propyldimethylsiloxy]-, 1-vinyl-, 1-allyl-, 1-[2-(cyclohexen-3-yl)ethyl]-, 1-[2(diphenylphosphino)ethyl]-, 1-[2(diphenylphosphino)propyl]-, 1-hydrido-, 1-[hydridodimethylsiloxy]-, 1-[2-(styryl)ethyldimethylsiloxy]-, 1-[(4-vinyl)phenyl]- and 1-[2-(styryl)ethyl]-substituted species.

Other examples of POSS monomers, include 1,3,5,7,9,11,13,15-[2-(chlorodimethylsilyl)ethyl]pentacyclo[9.5.1.13,9.15,15.17,13]octasiloxane; 1,3,5,7,9,11,13,15-[2-(chlorodimethylsilyl)ethyl]pentacyclo[9.5.1.13,9.15,15.17,13]octasiloxane; 1,3,5,7,9,11,13,15-[2-(dichlorodimethylsilyl)ethyl]pentacyclo[9.5.1.13,9.15,15.17,13]octasiloxane; 1,3,5,7,9-octavinyl-11,13,15-epoxyethylpentacyclo[9.5.1.13,9.1.15,15.17,13]octasiloxane; endo-3,7,14-tris[1-(3-dimethylsiloxy)propyloxy-2,3-epoxypropyl]-1,3,5,7,9,11,14,-heptacyclopentyltricyclo[7.3.3.1,5,11]-heptasiloxane; 1-(trimethylsiloxy)-1,3,5,9,11,13,15-heptacyclopentyl-7-[3-(methacryl)propyl]-7-methyltetracyclo[9.5.1.15,11.19,15]octasiloxane; 1,3,5,7,9-pentavinyl-11,13,15-[1-hydroxy-2-(methacryl)ethyl]pentacyclo[9.5.1.13,9.15,15.17,13]octasiloxane; 1,3,5,7,9,11-hexacyclohexyltetracyclo[5.5.1.13,11.15,9]hexasiloxane; 1,3,5,7,9,11,13,15-octacyclohexylpentacyclo[9.5.1.13,9.15,15.17,13]octasiloxane; 1,3,5,7,9,11,13,15-octacyclopentylpentacyclo[9.5.1.13,9.15,15.17,13]octasiloxane; 1,3,5,7,9,11,13,15-octaphenylpentacylo[9.5.1.13,9.15,15.17,13]octasiloxane; 1,3,5,7,9,11,13,15-octamethylpentayclo[9.5.1.13,9.15,15.17,13]octasiloxane; 1,3,5,7,9,11,13,15-octakis(di-methylsilyloxy)pentacyclo[9.5.1.13,9.15,15.17,13]octasiloxane; 1,3,3-(norbornenyldimethylsiloxy)-1,3,-dicyclohexyldisiloxane; 1,3,5,7,9,11,13,15-octavinylpentacyclo[9.5.1.13,9.15,15.17,13]octasiloxane; endo-3,7,14-tri(dimethylsilylhydrido)-1,3,5,7,9,11,14-heptacyclopentyltricyclo[7.3.3.15,11]heptasiloxane; 1,1,3,3-(hydridodimethylsiloxy)-1,3-dicyclohexyldisiloxane; endo-3,7,14-trihydroxy-1,3,5,7,9,11,14-heptacyclopentyltricyclo[7.3.3.15,11]heptasiloxane; endo-3,7,14-trihydroxy-1,3,5,7,9,11,14-heptacyclohexyltricyclo[7.3.3.15,11]heptasiloxane; 1,1,3,3-(tetrahydroxy)-1,3-dicyclohexyldisiloxane; 1,3,5,7-(tetrahydroxy)-1,3,5,7-(tetraphenyl)cyclotetrasiloxane; endo-7,14-dihydroxy-3-(3,3,3-trifluoropropyldimethylsiloxy)-1,3,5,9,11,13,15-heptacyclopentyltricyclo[7.3.3.15,11]octasiloxane; endo-7,14-dihydroxy-3-(3,3,3-trifluoropropyldimethylsiloxy)-1,3,5,9,11,13,15-heptacyclopentyltricyclo[7.3.3.15,11]octasiloxane, among others.

Thus a wide array of POSS monomers are currently available, which can participate in a variety of polymerization reactions, including, free radical, cationic and/or anionic polymerization reactions. As with the vinyl pyridine species above, when POSS monomers are copolymerized with low $T_g$ monomers (such as the above unsaturated hydrocarbon monomer species) or where they are otherwise included within copolymers containing low $T_g$ monomers, then the high hardness of the POSS monomers within the resulting copolymers tends to increase the hardness of the resulting copolymers (and thus polymeric regions containing the copolymers). Moreover, the presence of the POSS monomers within the resulting copolymers also tends to decrease the tack of the resulting copolymers, and thus that of polymeric regions containing the same (e.g., where polyisobutylene is present in the polymeric region). An advantage of using POSS monomers is that good strength, non-tackiness and excellent thermal stability can be imparted using only a small number of these units.

Furthermore, compared to unsaturated hydrocarbon monomer species (as well as many other monomer species), POSS monomers are relatively polar/hydrophilic. Hence the presence of POSS monomers within the copolymers may increase the overall polarity/hydrophilicity of the same (and thus polymeric regions containing the same). This increase in polarity/ hydrophilicity will affect various properties of the polymeric regions, including water uptake/swelling, drug diffusion and release, polymer/therapeutic interactions, and biocompatibility. Also, due to the cage-like structure of certain POSS monomers, the POSS monomers may act as a depot for therapeutic agents and provide the therapeutic agents with enhanced stability in some embodiments. This would allow, for example, for the inclusion, within a single polymeric region, of a first therapeutic agent that is sequestered in the POSS cages and another therapeutic agent that dispersed elsewhere within the polymeric region. In still other embodiments, the therapeutic agent is bound to the POSS units.

Hydroxystyrenes for use in conjunction with the present invention include protected and unprotected hydroxystyrene monomer species. Examples of protected hydroxystyrene monomer species include styrene species substituted with one or more functional groups that are stable under cationic polymerization conditions, but which are hydrolysable into hydroxyl groups under the influence of acids or bases. More specific examples of protected hydroxystyrene monomer species include styrene monomers containing: (a) one or more —O—R groups, wherein R is a hydrocarbon group, typically containing from 1 to 12 carbons, including branched alkyl groups, cycloalkyl groups and alkylaryl groups or (b) one or more groups, where $R_1$, $R_2$, $R_3$ can be the same or different and are hydrocarbon groups, typically containing from 1 to 4 carbons, including unbranched and branched alkyl groups. Still more specific examples of protected hydroxystyrene monomers include tert-butyl protected hydroxystyrene tert-butoxystyrene), benzyl protected hydroxystyrene (benzyloxystyrene), cyclohexyl protected hydroxystyrene (cyclohexoxystyrene), neopentyl protected hydroxystyrene (neopentoxystyrene), acetyl protected hydroxystyrene (acetoxystyrene), tert-butyldimethylsilyl protected hydroxystyrene (tert-butyldimethylsilyloxystyrene), benzyl protected hydroxystyrene (benzyloxystyrene), amino protected hydroxystyrene, carboxy protected hydroxy styrene, and so forth. Thus a wide range of protected hydroxystyrene monomer species are available for incorporation into copolymers for use in the present invention.

The hydroxyl and protected groups in the hydroxystyrene monomer species can be substituted, for example, at the 2-, 3- or 4-ring positions of the styrene, at the 2-, 3- or 2-, 4- or 3-, 4- or 3-, 5-positions, at the 2-, 3-, 4- or 3-, 4-, 5- or 2-, 4-, 5- or 2-, 5-, 6- or 3-, 5-, 6-positions, and so forth. In certain beneficial embodiments, the hydroxyl and protected groups are substituted at the 4-position.

Copolymers for use in the present invention include those containing 50 to 90 wt % unsaturated hydrocarbon monomer species and 10 to 50 wt % protected hydroxystyrene monomer species, unprotected hydroxystyrene monomer species, or a combination of the same.

When protected and/or unprotected hydroxystyrene monomer species are copolymerized with low $T_g$ monomers (such as the above unsaturated hydrocarbon monomer species) or where they are otherwise included within copolymers containing low $T_g$ monomers, then the high hardness that is associated with many of these monomer species can increase the hardness, as well as decrease the tack, of the resulting copolymers (and thus polymeric regions containing such copolymers), while retaining elastomeric properties of the low $T_g$ that are desirable in devices, especially those that expand. Furthermore, compared to unsaturated hydrocarbon monomer species (as well as many other monomer species), hydroxystyrene and various of the above protected hydroxystyrene monomer species are relatively polar/hydrophilic. Hence the presence of these monomers within the resulting copolymers tends to increase the overall polarity/hydrophilicity of the same (and thus polymeric regions containing the same). This increase in polarity/hydrophilicity will, in turn, affect various properties of the polymeric regions, including water uptake/swelling, drug diffusion and release, polymer/therapeutic interactions, and biocompatibility. Furthermore, in the case of hydroxystyrene, the presence of the phenolic groups on the resulting copolymers is expected to impart a degree of antioxidant properties to the material.

Vinyl alcohol has a published homopolymer $T_g$ of 85° C. Vinyl alcohol monomers are not directly polymerized via addition polymerization due to keto-enol tautomerism. However, polymers of vinyl alcohol can be prepared by other means as discussed below. High $T_g$ vinyl ethers for use in conjunction with the present invention include alkyl vinyl ethers and aryl-alkyl vinyl ethers which may include linear, branched and cyclic alkyl groups having from 1 to 12 carbon atoms. Specific examples include tert-butyl vinyl ether ($T_g$ 88° C.), neopentyl vinyl ether, cyclohexyl vinyl ether ($T_g$ 81° C.) and benzyl vinyl ether, as well as various mono-, di- and tri-alkylsilyl vinyl ethers, where the alkyl groups are preferably and independently, linear or branched alkyl groups containing from 1 to 4 carbon atoms, such as tert-butyldimethylsilyl vinyl ether. As discussed below, certain of these ethers are readily hydrolysable, whereas others are not.

Copolymers for use in the present invention include those containing 50 to 90 wt % unsaturated hydrocarbon monomer species and 10 to 50 wt % vinyl alcohol, high $T_g$ vinyl ethers, or a combination thereof.

When vinyl alcohol and/or high $T_g$ vinyl ethers are copolymerized with low $T_g$ monomers (such as the above unsaturated hydrocarbon monomer species) or where they are otherwise included within copolymers containing low $T_g$ monomers, then the higher hardness of the vinyl alcohol and/or high $T_g$ vinyl ethers within the resulting copolymers tends to increase the hardness of the same (and thus polymeric regions containing the same). Moreover, the presence of the vinyl alcohol and/or high $T_g$ vinyl ethers within the resulting copolymers may also tend to decrease the tack of the resulting copolymers, and thus that of polymeric regions containing the same (e.g., in instances where polyisobutylene is present in the polymeric regions). Furthermore, compared to unsaturated hydrocarbon monomer species (as well as many other monomer species), vinyl alcohol and the above vinyl ethers are relatively polar/hydrophilic. Hence the presence of vinyl alcohol and/or high $T_g$ vinyl ethers within the resulting copolymers will commonly increase the overall polarity/hydrophilicity of the same (and thus polymeric regions containing the same). This increase in polarity/hydrophilicity will affect various properties of the polymeric regions, including water uptake/swelling, drug diffusion and release, polymer/therapeutic interactions, and biocompatibility.

Various polymerization techniques can be used to form the above copolymers, including anionic, cationic and radical polymerization methods, both living and non-living.

For instance, many unsaturated hydrocarbon monomers, including several of those described above (e.g., isobutylene, 2-methylbutene, and the like) as well as various vinyl ether monomer species, protected hydroxystyrene monomer species, and certain POSS monomers (depending upon the attached reactive group), are cationically polymerizable. Hence these monomers may be cationically polymerized in combination with other cationically polymerizable monomers, either concurrently (leading, for example, to alternating, random, statistical or gradient copolymers) or sequentially (leading, for example, to block copolymers).

In certain embodiments where sequential cationic polymerization reactions are carried out, a capping species may be provided after the first cationic polymerization reaction is conducted and before the second cationic polymerization reaction, for example, due to drastically different reactivities between the species being polymerized in the first and second cationic polymerization reactions.

As a specific example, U.S. Ser. No. 10/902,280, filed Jul. 29, 2004, describes a method whereby a carbocationically terminated polymer containing one or more olefin blocks is contacted with a capping species to form an end-capped carbocationically terminated polymer, which is subsequently contacted with one or more vinyl ether monomer species, forming a polyvinyl ether segment. As noted above, certain polymerized vinyl ether monomers have groups that are readily hydrolyzed to alcohol groups under the influence of acids or bases. Examples of vinyl ether monomer species that are readily hydrolyzed include tert-butyl vinyl ether, benzyl vinyl ether and tert-butyldimethylsilyl vinyl ether. In some cases, the copolymers include a plurality of units that correspond to readily hydrolysable vinyl ether monomer and/or vinyl ether monomer species that are not readily hydrolysable, examples of which include cyclohexyl vinyl ether and neopentyl vinyl ether. Specific polymers described in U.S. Ser. No. 10/902,280 include poly(t-butyl vinyl ether)-polyisobutylene-poly(t-butyl vinyl ether) triblock copolymer and poly(t-butyldimethylsilyl vinyl ether)-polyisobutylene-poly(t-butyldimethylsilyl vinyl ether) triblock copolymer, which are hydrolysable into poly(vinyl alcohol)-polyisobutylene-poly(vinyl alcohol) triblock copolymer, and poly(cyclohexyl vinyl ether-co-t-butyl vinyl ether)-polyisobutylene-poly(cyclohexyl vinyl ether-co-t-butyl vinyl ether) triblock copolymer, which is hydrolysable into poly(cyclohexyl vinyl ether-co-vinyl alcohol)-polyisobutylene-poly(cyclohexyl vinyl ether-co-vinyl alcohol) triblock copolymer.

As another example, U.S. Ser. No. 10/776,674 filed Feb. 11, 2004 describes a process in which a carbocationically terminated polymer containing one or more olefin blocks is contacted with a capping species to form an end-capped carbocationically terminated polymer, which is then contacted with a capped hydroxystyrene monomer species which undergoes further cationic polymerization. Specific polymers described in U.S. Ser. No. 10/776,674 include polyisobutylene-poly(4-tert-butyldimethylsilyloxystyrene) diblock copolymer, poly(4-tert-butyldimethylsilyloxystyrene)-polyisobutylene-poly(4-tert-butyldimethylsilyloxystyrene) triblock copolymer, the hydrolysis of the same to form poly(4-hydroxystyrene)-polyisobutylene-poly(4-hydroxystyrene) triblock copolymer, poly(4-tert-butoxystyrene)-polyisobutylene-poly(4-tert-butoxystyrene) triblock copolymer, as well as the hydrolysis of the same to form poly(4-hydroxystyrene)-polyisobutylene-poly(4-hydroxystyrene) triblock copolymer.

It is also possible to form copolymers that contain cationically polymerizable monomers with monomers that are not cationically polymerizable. For example, as described in U.S. Ser. No. 10/872,134, cationic polymerization, preferably a living cationic polymerization, can first be carried out, e.g., on an unsaturated hydrocarbon monomer, followed by the conversion of the resulting cationically terminated polymer into an anionically terminated polymer, which can then participate in an anionic polymerization step, preferably a living anionic polymerization step. Anionically polymerizable monomers for this purpose include polar monomers, such as vinyl pyridines, conjugated dienes such as isoprene, butadiene and the like, and certain POSS monomers (depending on the reactive groups).

Conversely, anionically polymerizable monomers such as those above can polymerized copolymerized with other anionically polymerizable monomers, either concurrently or sequentially. Moreover, anionic polymerization can first be conducted, followed by conversion of the resulting polymer with a capping species into a polymer that can participate in another type of polymerization, for example, cationic or free radical polymerization.

In addition to polymerization techniques such as those discussed above (including methods in which a first polymer is formed in a first polymerization process followed by one or more further polymerization processes), block copolymers can also be readily formed by linking previously formed polymer blocks together using appropriate linking chemistries.

Hence, using the above and other techniques, various copolymers for use in the present invention can be formed, which copolymers, again, include (a) one or more unsaturated hydrocarbon monomer species and (b) one or more heteroatom-containing monomer species.

In addition to the above copolymers, the polymeric regions for use in conjunction with the present invention also optionally contain additional polymers, which can be, for example, blended with or attached to the above copolymers.

Examples of polymers which can be attached to and/or blending with the copolymers include a variety of homopolymers and copolymers (including alternating, random, statistical, gradient and block copolymers), which may be cyclic, linear or branched (e.g., the polymers may have star, comb or dendritic architecture), which may be natural or synthetic, and which may be thermoplastic or thermosetting. Specific polymers may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

The additional polymer chains can be provided for various reasons. For instance, additional chains may be introduced (a) to render the polymeric release region more hydrophilic (or more hydrophobic), (b) to modulate the release profile of the therapeutic agent, if any (c) to affect one or more of the mechanical characteristics, tackiness, biostability, biocompatibility, material processability, and so forth.

As noted above, the medical devices of the present invention also optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in conjunction with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Particularly beneficial non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat.

No. 5,733,925 assigned to NeoRx Corporation, the entire disclosure of which is incorporated by reference.

Where a therapeutic agent is included, a wide range of therapeutic agent loadings can be used in conjunction with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric region(s), and the nature of the medical device, among other factors.

Numerous techniques are available for forming polymeric regions in accordance with the present invention.

For example, where the polymeric region is formed from one or more polymers having thermoplastic characteristics, a variety of standard thermoplastic processing techniques may be used to form the polymeric region, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire devices or portions thereof can be made.

In other embodiments, solvent-based techniques are used to form the polymeric regions of the present invention. Using these techniques, a polymeric region can be formed by first providing a solution that contains the polymer(s) that form the polymeric region and subsequently removing the solvent. The solvent that is ultimately selected will contain one or more solvent species, which are generally selected based on their ability to dissolve the polymer(s) that form the polymeric region, as well as other factors, including drying rate, surface tension, etc. Generally, several solvents will be tested to see which provides polymeric regions having the best characteristics. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or polymer melt (where thermoplastic processing is employed) is applied to a substrate to form a polymeric region. For example, the substrate can correspond to all or a portion of an implantable or insertable medical device to which a polymeric region is applied. The substrate can also be, for example, a template, such as a mold, from which the polymeric region is removed after solidification. In other embodiments, for example, extrusion and co-extrusion techniques, one or more polymeric regions are formed without the aid of a substrate. In a more specific example, an entire stent body is extruded. In another, a polymeric layer is co-extruded along with and underlying stent body. In another, a polymeric layer is provided on an underlying step body by spraying or extruding a coating layer onto a pre-existing stent body. In yet another more specific example, a stent is cast in a mold.

If it is desired to provide one or more therapeutic agents (and/or any other optional agents) within the polymeric region, so long as these agents are stable under processing conditions, then they can be provided within the polymer containing solution or polymer melt and co-processed along with the polymer(s).

Alternatively, therapeutic and/or other optional agents can be introduced subsequent to the formation of the polymeric region in some embodiments. For instance, in some embodiments, the therapeutic and/or other optional agents are dissolved or dispersed within a solvent, and the resulting solution contacted with a previously formed polymeric region (e.g., using one or more of the application techniques described above, such as dipping, spraying, etc.).

As noted above, barrier regions are provided over therapeutic-agent-containing regions in some embodiments of the invention. In these embodiments, a polymeric barrier region can be formed over a therapeutic-agent-containing region, for example, using one of the solvent based or thermoplastic techniques described above. Alternatively, a previously formed polymeric region can be adhered over a therapeutic agent containing region.

Although various embodiments are specifically illustrated and described herein, it will be appreciated that modifications and variations of the present invention are covered by the above teachings and are within the purview of the appended claims without departing from the spirit and intended scope of the invention.

EXAMPLES

Example 1

Preparation of Polyisobutylene-POSS Diblock Copolymer 1-chloro-1-(4-methyphenyl)ethane (p-MeStCl) and 5-tert-butyl-1,3-bis-(1-chloro-1-methylethyl)-benzene (tBuDiCumCl) are prepared as previously described. Cao, X.; Faust, R. *Macromolecules* 1999, 32(17), 5487; Györ, M.; Wang, H.-C.; Faust, R. *J. Macromol. Sci.-Pure Appl. Chem.* 1992, A29, 639. Divinylbenzene (DVB, tech., 80%, Aldrich), cuprous chloride (98+%, Aldrich), trisilanol-cyclopentyl-POSS (Hybrid Plastics), trichlorosilane (Aldrich), methylcyclohexane (MeChx, 99% anhydrous, Aldrich), 2,6-di-tert-butylpyridine (DTBP, 99.4% by GC, Aldrich), and Titanium (IV) chloride ($TiCl_4$, 99.9%, Aldrich) are used as received. Tetrahydrofuran (THF) is purified by distillation under nitrogen from sodium and triethylamine (TEA) is distilled under nitrogen from calcium hydride.

2,4,4-trimethyl-2-chloropentane (TMPCl) may be prepared by hydrochlorination of 2,4,4-trimethyl-1-pentene (Fluka, 98%) with hydrogen chloride gas in dry dichloromethane at 0° C. See, Kaszas, G.; Gyor, M.; Kennedy, J. P.; Tüdös, F. *J. Macromol. Sci., Chem* 1983, A18, 1367-1382.

Methyl chloride ($CH_3Cl$)(MeCl) and isobutylene (Matheson) are passed through in-line gas purifier columns packed with BaO/Drierite.

p-Divinylbenzene. p-DVB is separated from commercially available 80% DVB (20% ethylvinylbenzene containing diethylbenzene, 56% m- and 24% p-DVB) according to the literature. Popov, G.; Schwachula, G. German Patent 118059; Wiley, R.; Jin, J-I.; Kamath, Y.; *J. Polym. Sci., Polym. Chem. Ed.* 1968, 6(4), 1065. Commercial DVB (50 g), toluene (100 mL), methanol (2 mL) and hydroquinone (0.1 g) are heated to 80° C. Cuprous chloride (60 g) is added to the reaction mixture, with stirring, followed by slow cooling to 25° C. over a period of 4 h. The solid complex is immediately filtered at 25° C. and washed several times with toluene. The p-isomer-copper complex is decomposed by heating to 80° C. in the presence of toluene (60 mL) and hydroquinone (0.1 g), stirred at this temperature for 30 min followed by hot filtration. Concentration of the filtrate in vacuo produced a clear mixture with the p-DVB content. For further purification, a sample is partially crystallized by cooling to 5° C. and the unfrozen liquid is decanted. The obtained product contained 0.64% ethylvinylbenzene, 3.46% m- and 96.00% p-DVB.

(Styrylethyl)-trichlorosilane is first synthesized by a platinum-catalyzed mono-hydrosilylation of p-DVB with chlorodimethylsilane in hexane. Kim, I-J.; Faust, R. *Polym. Prepr., (Am. Chem. Soc. Div. Polym. Chem)* 2000, 41(2), 1309. A styryl-POSS macromer is then prepared by corner capping reaction of incompletely condensed trisilanol (c-$C_5H_9$)$_7$Si$_7$O$_9$(OH)$_3$ with (styrylethyl)-trichlorosilane, according to the procedure reported in Haddad, T. S.; Lichtenhan, J. D. *Macromolecules* 1996, 29, 7302.

Figure 1:
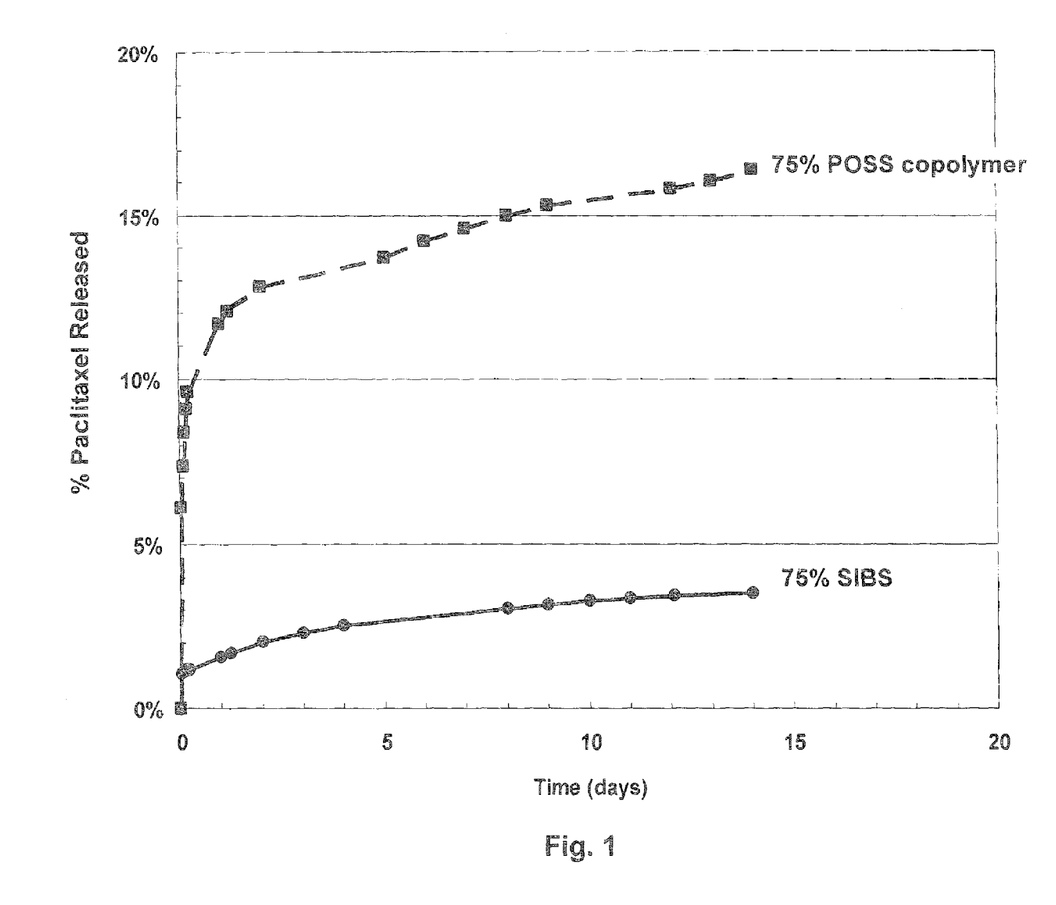
FIG. 1 is a plot of cumulative release of paclitaxel for coatings containing (a) 25 wt % paclitaxel and 75 wt % polystyrene-polyisobutylene-polystyrene triblock copolymer (SIBS) and (b) 25 wt % paclitaxel and 75 wt % POSS copolymer.
Figure 2:
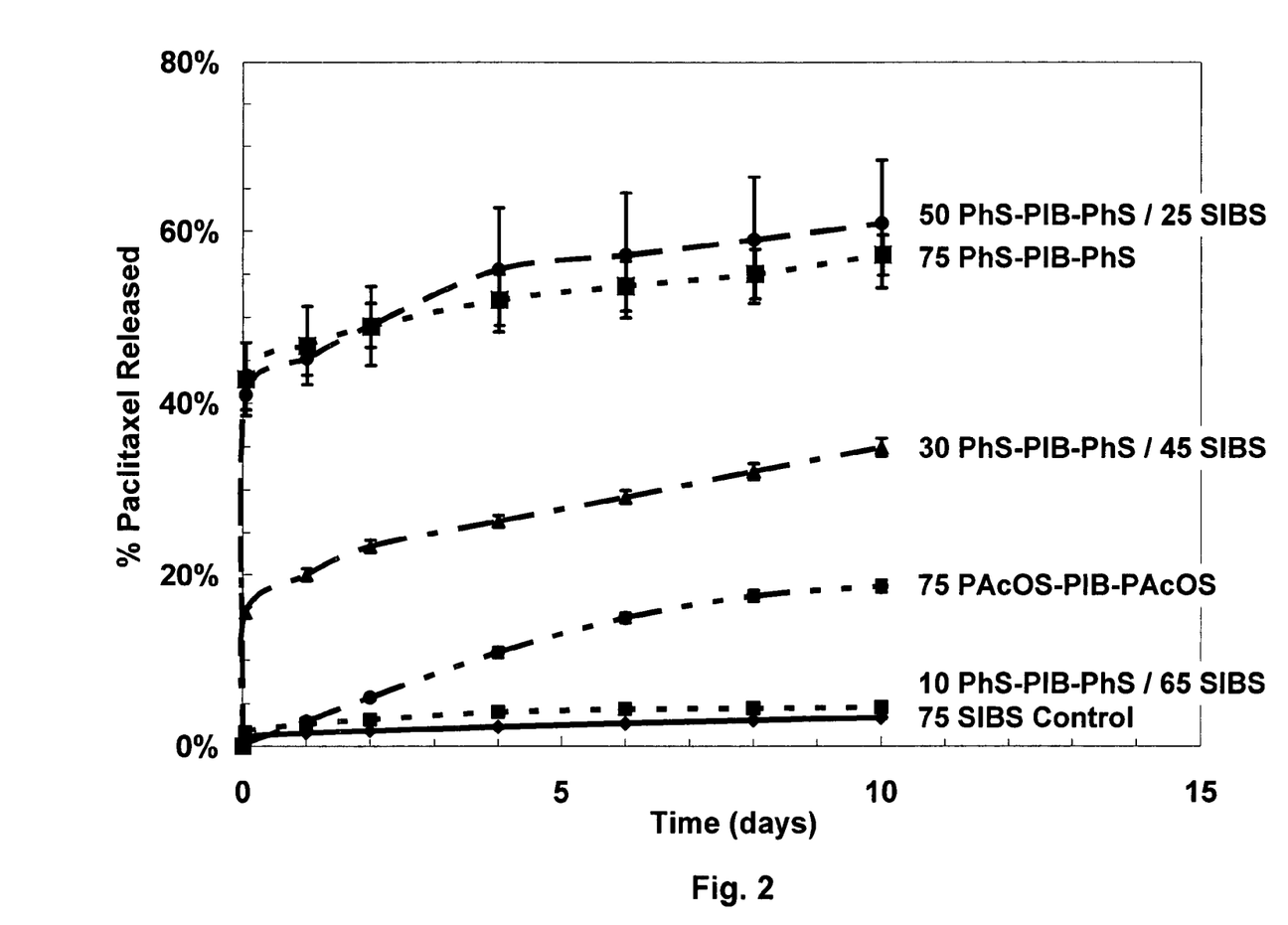
FIG. 2 is a plot of cumulative release of paclitaxel for coatings containing: (a) 25 wt % paclitaxel and 75 wt % polystyrene-polyisobutylene-polystyrene triblock copolymer, (b) 25 wt % paclitaxel and 75 wt % poly(p-hydroxystyrene)-polyisobutylene-(p-hydroxystyrene) triblock copolymer, (c) 25 wt % paclitaxel and 50 wt % poly(p-hydroxystyrene)-polyisobutylene-(p-hydroxystyrene) triblock copolymer and 25 wt % SIBS, (d) 25 wt % paclitaxel, 30 wt % poly(p-hydroxystyrene)-polyisobutylene-(p-hydroxystyrene) triblock copolymer and 45 wt % SIBS, (e) 25 wt % paclitaxel and 10 wt % poly(p-hydroxystyrene)-polyisobutylene-(p-hydroxystyrene) triblock copolymer and 65 wt % SIBS, (f) 25 wt % paclitaxel and 75 wt % poly(p-acetoxystyrene)-polyisobutylene-(p-acetoxystyrene) triblock copolymer.
Figure 3:
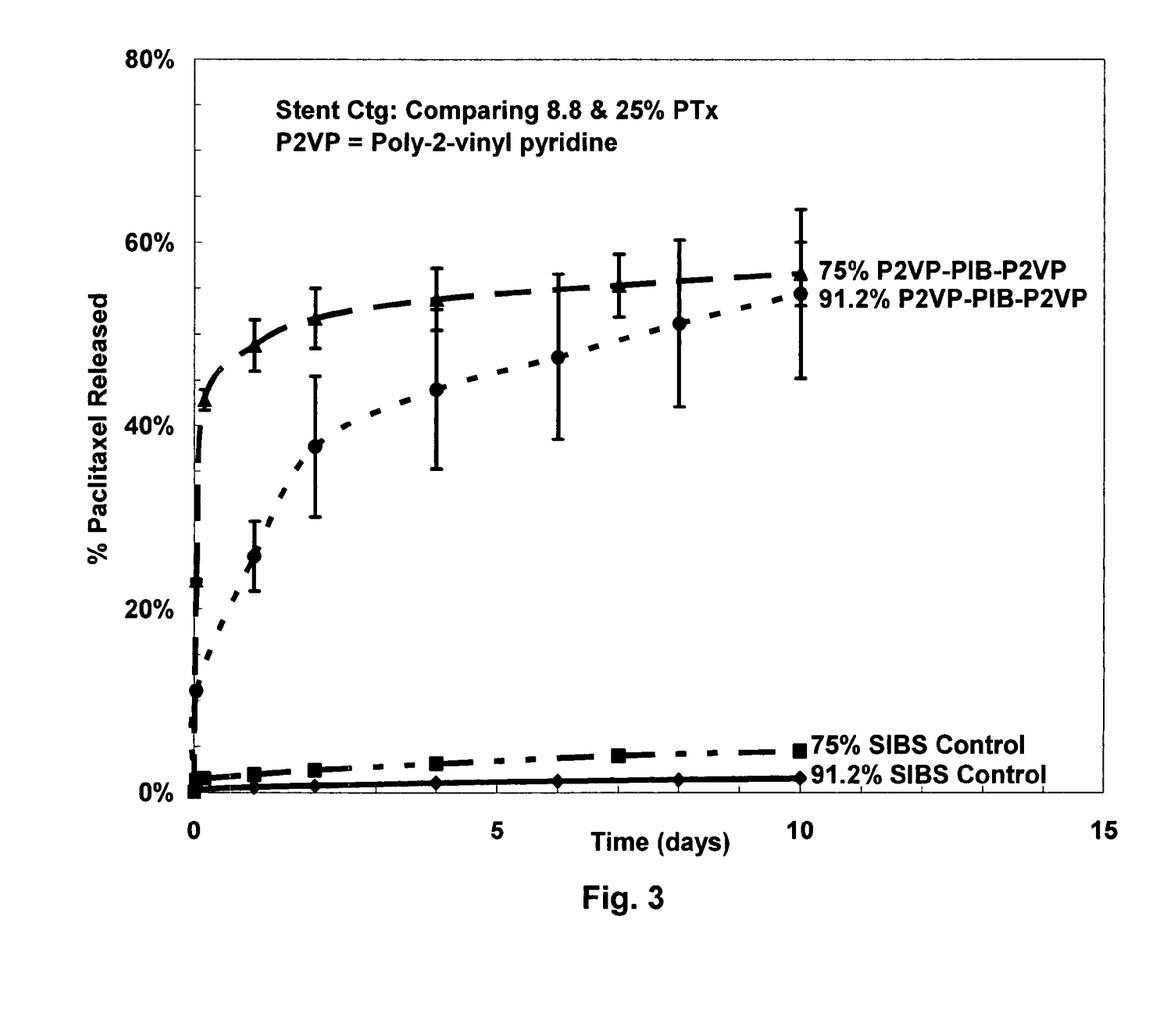
FIG. 3 is a plot of cumulative release of paclitaxel for coatings containing: (a) 25 wt % paclitaxel and 75 wt % SIBS, (b) 8.8 wt % paclitaxel and 91.2 wt % SIBS, (c) 25 wt % paclitaxel and 75 wt % poly(2-vinyl pyridine)-polyisobutylene-(2-vinyl pyridine) triblock copolymer, and (d) 8.8 wt % paclitaxel and 91.2 wt % poly(2-vinyl pyridine)-polyisobutylene-(2-vinyl pyridine) triblock copolymer.
Figure 4:
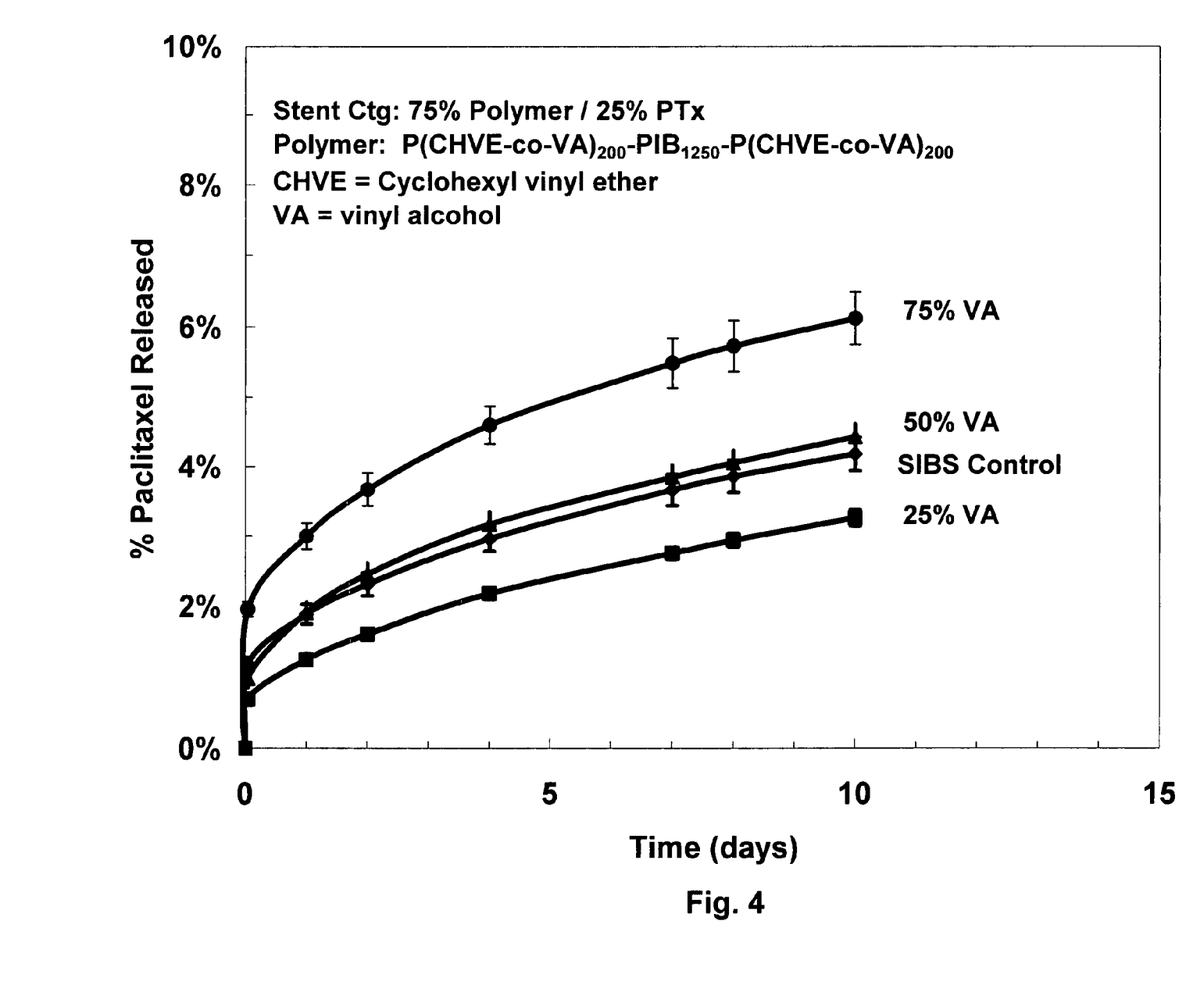
FIG. 4 is a plot of cumulative release of paclitaxel for coatings containing: (a) 25 wt % paclitaxel and 75 wt % SIBS, (b) 25 wt % paclitaxel and 75 wt % poly(cyclohexyl vinyl ether-co-vinyl alcohol)-polyisobutylene-poly (cyclohexyl vinyl ether-co-vinyl alcohol) triblock copolymer (with endblocks containing 25 mol % vinyl alcohol), (c) 25 wt % paclitaxel and 75 wt % poly(cyclohexyl vinyl ether-co-vinyl alcohol)-polyisobutylene-poly(cyclohexyl vinyl ether-co-vinyl alcohol) triblock copolymer (with endblocks containing 50 mol % vinyl alcohol), and (d) 25 wt % paclitaxel and 75 wt % poly(cyclohexyl vinyl ether-co-vinyl alcohol)-polyisobutylene-poly(cyclohexyl vinyl ether-co-vinyl alcohol) triblock copolymer (with endblocks containing 75 mol % vinyl alcohol).

The synthesis of poly{(IB-b-(styryl-POSS)} diblock copolymer is achieved by living cationic sequential block copolymerization. The living cationic polymerization of IB is carried out first using 2,4,4-trimethyl-2-chloropentane (TMPCl)/TiCl$_4$/MeChx:CH$_3$Cl (60:40, v:v)/−80° C. system in the presence of DTBP. Typical concentrations of reactants are as follows: [TMPCl]=0.002 M, [TiCl$_4$]=0.036 M, [DTBP]= 0.003 M, and [IB]=0.075 M. When the reaction reaches 100% conversion (1 h), styryl-POSS is introduced within 2 min after the addition of additional TiCl$_4$ (0.072 M) into the reactor in order to increase the polymerization rate of styryl-POSS macromer. As shown in FIG. 2, GPC analysis of the diblock copolymer confirms efficient chain extension of styryl-POSS from living PIB and a well-defined diblock copolymer is prepared with ~100% crossover efficiency. Molecular weight of the poly(IB-b-(styryl-POSS)) copolymer obtained from the GPC analysis is close to theoretical predictions ($M_{n\ GPC}$=22000 vs $M_{n\ theoretical}$=23000).

As may become more clear upon the additional examples below, a triblock copolymer may be synthesized using a difunctional initiator such as 5-tert-butyl-1,3-bis-(1-chloro-1-methylethyl)-benzene (tBuDiCumCl) in the above procedure, a star copolymer may be synthesized using a trifunctional initiator, and so forth.

Example 2

Synthesis of Poly(hydroxystyrene)-b-PIB-b-Poly(hydroxystyrene) Triblock Copolymer 4-(tert-butyldimethylsilyloxy)styrene (TBDMSt) is prepared from 4-acetoxystyrene according to the literature. Hirai, A.; Yamaguchi, K.; Takenaka, K.; Suzuki, K.; Nakahama, S. *Makromol. Chem., Rapid Commun.* 1982, 3, 941. It is freshly distilled from CaH$_2$ in vacuum before the polymerization using phenothiazine (1-2 mg) inhibitor. 4,4'-dimethyl-1,1-diphenylethylene (ditolyl ethylene or DTE) is synthesized according to the literature. Hadjikyriacou, S.; Faust, R., *Macromolecules* 1996, 29, 5261. Titanium(IV) isopropoxide, Ti(OiPr)$_4$ (Aldrich, 99.999%) is used as received.

For the synthesis of poly(4-tert-butyldimethylsilyloxystyrene)-b-PIB-b-poly(4-tert-butyldimethylsilyloxystyrene) triblock copolymers, 5-tert-butyl-1,3-dicumylchloride (tBudiCumCl) is used as initiator. In the case of sample A and B (Table 1), IB is polymerized using the following concentrations: [tBudiCumCl]=0.001 M, [IB]=1.60 M, [DTBP]=0.006 M, [TiCl$_4$]=0.036 mol/L. In the case of sample C the concentration of tBudiCumCl is 0.002 M, and the other concentrations remains the same. The order of the addition is: MeChx (9.7 mL, 8.7 mL in sample C), MeCl (9.2 mL), tBudiCumCl (1.0 mL, 0.025 M in MeChx, 2.0 mL in case of sample C), DTBP (1.0 mL, 0.15 M in MeChx), IB (3.12 mL) and TiCl$_4$ (2.0 mL, 0.454 M in MeChx/MeCl, 60/40 v/v). IB is polymerized for 90 minutes and then DTE stock solution (1.0 mL, 0.1 M in MeChx/MeCl, 60/40 v/v, 2.0 mL in case of sample C) is added and the mixture left for 60 minutes. After the capping reaction Ti(OiPr)$_4$ solution (2.8 mL, 0.25 M in MeChx/MeCl, 60/40, v/v) is added and stirred thoroughly. 2.928 g (sample A) and 1.464 g (samples B and C) 4-(tert-butyldimethylsilyloxy)styrene monomer are measured out and made up to 7 mL solution in MeChx/MeCl 60/40 v/v solvent mixture and poured into the polymerization mixture under vigorous stirring. The monomer is polymerized for 30 minutes. The polymerization is terminated by prechilled methanol, and the polymer is precipitated into large excess methanol (~200 mL). The precipitation is repeated from THF into methanol. The mixture is left overnight, the solvent is decanted and the polymer is dried in vacuum. Table 1 shows the characteristics of certain triblock copolymers.

TABLE 1

| Sample | Designed $M_n$ PIB | Designed $M_n$ PTBDMSt | PIB (GPC) $M_n$ | PIB (GPC) PDI | Triblock (GPC) $M_n$ | Triblock (GPC) PDI | PTBDMSt* Conv. (%) | PTBDMSt* mol % |
|---|---|---|---|---|---|---|---|---|
| A | 90,000 | 117,100 | 89,500 | 1.07 | 176,300 | 1.10 | 92.7 | 23.0 |
| B | 90,000 | 58,500 | 88,400 | 1.08 | 132,100 | 1.10 | 89.5 | 13.1 |
| C | 45,000 | 29,300 | 48,300 | 1.08 | 74,200 | 1.09 | 90.3 | 13.3 |

*PTBDMSt = poly(4-tert-butyldimethylsilyloxystyrene)

Poly(4-tert-butyldimethylsilyloxystyrene)-b-PIB-b-poly(4-tert-butyldimethylsilyloxystyrene) triblock copolymer is hydrolyzed as follows. 2.5 g of the above copolymer (e.g., $M_n$=146,000, 87.0 mol % PIB) is dissolved in 250 mL THF (anhydrous) at room temperature. 10 mL tetrabutylammonium fluoride (1.0 M in THF) is added and the solution is refluxed overnight under stirring. The solution is slightly hazy. After 14 hours, the solution is cooled down and precipitated into 1 L water. The precipitation is repeated from THF into 1 L water. The polymer is filtered off, dried in vacuum and extracted with pentane in a Soxhlet Extractor. After the extraction, the polymer is dried again in vacuum.

Example 3

Synthesis of poly(p-acetoxystyrene)-polyisobutylene-(p-acetoxystyrene) triblock copolymer 1 g of poly(4-tert-butyldimethylsilyloxystyrene)-b-PIB-b-poly(4-tert-butyldimethylsilyloxystyrene) triblock copolymer from Example 2 is dissolved in 15 mL anhydrous THF. Then, 1.42 mL (15 mmol) distilled acetic anhydride (Aldrich), 1.21 mL (15 mmol) pyridine (Aldrich) and 122 mg (1 mmol) 4-dimethylaminopyridine (Aldrich) are added. The resulting homogenous solution is left for one day at room temperature. The polymer solution is poured into water (200 mL) and the precipitated polymer is washed thoroughly with water, filtered and dried in vacuum.

Example 4

Synthesis of poly(2-vinyl pyridine)-polyisobutylene-poly(2-vinyl pyridine) triblock copolymer 2.6-Di-tert-butylpyridine (Aldrich. 97%) is purified by distillation from $CaH_2$. Isobutylene (Air Gas) is passed through in-line gas purifier columns packed with $CaSO_4$ and no. 13 molecular sieves and condensed at $-15°$ C. prior to polymerization.

Methyl chloride ($CH_3Cl$) is passed through in-line gas purifier columns packed with BaO/Drierite and condensed at $-80°$ C. prior to polymerization. Methylene chloride ($CH_2Cl_2$) is purified by washing it with 10% aqueous NaOH and then with distilled water until neutral and dried over anhydrous $MgSO_4$ overnight. It is refluxed for 24 h and distilled from $CaH_2$, just before use. n-Hexane is rendered olefin free by refluxing it over concentrated sulfuric acid for 48 h. It is washed with 10% aqueous NaOH and then with deionized water until neutral and stored over $MgSO_4$ for 24 h. It is refluxed over $CaH_2$ overnight and distilled. Tetrahydrofuran (Merck p.a.) is purified first by distillation under nitrogen from $CaH_2$ and then by refluxing over potassium. n-Butyllithium (n-BuLi, 2.5 M in hexane) is purchased from Aldrich and its concentration is titrated by a standard method. See, e.g., Reed, P. J.; Urwin, J. R. *J. Organometal. Chem.* 1972, 39, 1-10. 1,4-Bis(1-phenylethenyl)benzene is synthesized using procedures like that described in U.S. Pat. No. 4,182,818 to Tung, L. H. and Lo, G. Y.-S. 1,1-Diphenylethylene purchased from Aldrich Chemical Co. is purified by vacuum distillation under potassium metal.

The preparation of 1,1-diphenylhexyllithium is carried out under high vacuum conditions ($<10^{-6}$ mbar). 0.037 g of n-butyllithium ($5.7 \times 10^{-4}$ mol) is added at $-78°$ C. to a reactor containing 0.01 mL of 1,1-diphenylethylene ($5.7 \times 10^{-5}$ mol) dissolved in tetrahydrofuran. After 5 minutes, the cherry-reddish solution is brought to room temperature for 1 hour. During this step, unreacted n-butyllithium is decomposed by the reaction with tetrahydrofuran. The solution is delivered into a graduated cylinder with a stopcock, which is stored in a refrigerator.

2-vinyl pyridine is obtained from Aldrich.

The preparation of a difunctional macromonomer ($\alpha,\omega$1,1-diphenylethylene end-functionalized polyisobutylene) is carried out at $-80°$ C. under nitrogen atmosphere. To a prechilled 500 mL 3-neck flask equipped with mechanical stirrer are added sequentially 187 mL of hexane, 111 mL of methyl chloride, 0.086 g of 5-tert-butyl-1,3-bis(1-chloro-1-methylethyl)benzene (tBuDiCumCl) ($3.0 \times 10^{-4}$ mol), 0.2 mL of 2,6-di-tert-butylpyridine (DTBP) ($9.0 \times 10^{-4}$ mol), and 21 mL of isobutylene (IB) (0.27 mol). Then, 1.2 mL of titanium tetrachloride ($1.1 \times 10^{-2}$ mol) is added into the reactor to polymerize the isobutylene. After the completion of monomer polymerization, 0.34 g of 1,4-bis(1-phenylethenyl)benzene ($1.2 \times 10^{-3}$ mol) dissolved in methylene chloride is added into the reactor. After 2 hours, 5.15 g of dimethylzinc (Aldrich) ($5.4 \times 10^{-2}$ mol) dissolved in toluene is added into the reactor. 2 hours later, 30 mL of prechilled methanol is added into the reactor to quench the reaction. The polymer solution is then poured into ammonium hydroxide/methanol (10/90, v/v). After the evaporation of solvents, the polymer is dissolved in hexane and inorganics are filtered. The polymer recovered by the precipitation of the polymer solution into methanol. The polymer is then dissolved again in hexane and recovered again by the precipitation of the polymer solution into methanol, followed by drying in a vacuum.

$^1$H NMR spectroscopy is carried out on a Bruker AC-250 MHz spectrometer at 25° C. in $CDCl_3$. Gel Permeation Chromatography (GPC) is carried out using a Waters HPLC system equipped with model 510 HPLC pump, model 410 differential refractometer, model 486 UV/visible detector, model 712 sample processor, and five ultra-Styragel columns connected in the series (500, $10^3$, $10^4$, $10^5$ and 100 Å). THF is used as an eluent at a flow rate of 1 mL/min.

According to $^1$H NMR and GPC measurements, functionalization and methylation at polyisobutylene chain ends are essentially complete. Essentially no change in the number average molecular weight and polydispersity of the 1,1-diphenylethylene functional polyisobutylene is observed, relative to those of the polyisobutylene precursor (Table 1), confirming that coupling reactions are virtually nonexistent.

TABLE 1

| Polymer | $M_n$ | $M_w/M_n$ |
| --- | --- | --- |
| Polyisobutylene | 55000 | 1.03 |
| $\alpha,\omega$-1,1-Diphenylethylene end-functional polyisobutylene | 56800 | 1.04 |

For the synthesis of poly(2-vinyl pyridine)-polyisobutylene-poly(2-vinyl pyridine) triblock copolymer, all chemical purifications and anionic polymerizations are carried out under high vacuum condition ($<10^{-6}$ mbar). 1.50 g ($2.6 \times 10^{-5}$ mol) of $\alpha,\omega$-1,1-diphenylethylene end-functionalized polyisobutylene (e.g., $M_n$=56800, see above) in 200 mL of hexane is stirred over calcium hydride for 24 hours. The polymer solution is then filtered to remove calcium hydride. Solvent is evaporated, and 87 mL of tetrahydrofuran is added to the remaining polymer. The polymer solution is then added to a reactor equipped with a stirrer, and 1,1-diphenylhexyllithium in tetrahydrofuran (see above) is added into reactor dropwise until the color of the polymer solution changes from colorless to yellowish. The amount of 1,1-diphenylhexyllithium used for this purpose is 0.0010 g ($4.1 \times 10^{-6}$ mol). The polymer solution is subsequently cooled to $-78°$ C. with vigorous stirring. After 10 minutes at this temperature, 0.01 g of n-butyllithium ($1.6 \times 10^{-4}$ mol) in 33 mL of hexane is added into the reactor. After an additional 12 hours, the polymer solution is heated to 40° C. and kept at this temperature for 1 hour. The polymer solution is then cooled down to $-78°$ C. After 10 minutes at this temperature, 1.19 mL 2-vinyl pyridine ($1.1 \times 10^{-2}$ mol) is distilled into the reactor. 40 minutes later, purified methanol is added to reactor to quench the reaction. The polymer solution is poured into methanol to yield a white solid polymer.

The block copolymer is purified by using hexane to remove polyisobutylene homopolymer. According to GPC and $^1$H NMR measurements, the purified block copolymer had an apparent $M_n$=67000, a $M_w/M_n$=1.11, and the composition of isobutylene and 2-vinylpyridine in the polymer is 68/32 w/w.

Example 5

Poly(cyclohexyl vinyl ether-co-vinyl alcohol)-Polyisobutylene-Poly(cyclohexyl vinyl ether-co-vinyl alcohol) Triblock Copolymer Synthesis Poly(cyclohexyl vinyl ether-co-tert-butyl vinyl ether)-b-polyisobutylene-b-poly(cyclohexyl vinyl ether-co-tert-butyl vinyl ether) triblock copolymers are synthesized by using tert-butyl-dicumylchloride (tBudiCumCl) as initiator. The reaction conditions are the following: temperature=−80° C., [tBudiCumCl]=0.001 M, [IB]=1.25 M, [DTBP]=0.004 M, [TiCl$_4$]=0.036 M, solvent: methyl chloride/hexane (CH$_3$Cl/Hex) 40/60 v/v mixture. At the end of the IB polymerization (generally 100% conversion), DTE is added at a concentration of 0.004 M and allowed to react for 1 hour. It is followed by the introduction of Ti(OiPr)$_4$ to reach a [Ti(OiPr)$_4$]/[TiCl$_4$] ratio of 1.6. Depending on the final monomer content of the copolymer, cyclohexyl vinyl ether (CHVE) and tert-butyl vinyl ether (tBVE) monomers are added in one of the three following amounts: (1) [CHVE]=0.15M and [tBVE]=0.05M), (2) [CHVE]=0.1M and [tBVE]=0.1 M, or (3) [CHVE]=0.05M and [tBVE]=0.15M, and the monomers are then polymerized for 2 hours to ensure essentially 100% conversion. Thus the end blocks consisted of 75% of tBVE and 25% of CHVE. The center PIB block had a M$_n$ of 67.4 kg/mol (PDI=1.09). The triblock copolymer had narrow molecular weight distribution (PDI=1.11) and exhibited good characteristics of a thermoplastic elastomer. By varying the monomer species concentration, triblock copolymers can be prepared with different lengths and compositions of end blocks.

The poly(CHVE-co-tBVE)-PIB-poly(CHVE-co-tBVE) triblock copolymers are then formed by first dissolving 2.0 g of the triblock copolymer in 200 mL methylene chloride, which is rendered moisture free by distilling it from phosphorus pentoxide. Dry nitrogen is passed through the polymer solution to remove oxygen dissolved in it. The temperature is controlled at 0° C. using the ice/water bath. Dry HBr gas is bubbled slowly through the solution for 20 min. The reaction mixture is then poured into a large amount of ammoniacal methanol and dried under the hood. The content is washed repeatedly with methanol and dried under vacuum. The product is poly(cyclohexyl vinyl ether-co-vinyl alcohol)-b-polyisobutylene-b-poly(cyclohexyl vinyl ether-co-vinyl alcohol), as characterized by $^{13}$C NMR and FT-IR.

Example 6

Paclitaxel Elution from Coated Stents

Stent coating solutions are provided that contain 99 wt % solvent mixture containing 25 wt % THF and 74 wt % toluene, 0.25 wt % paclitaxel and 0.75 wt % polymer. All solutions are prepared by mixing the polymer, solvent and paclitaxel, thoroughly mixing (e.g., overnight), and filtering.

The following polymer solutions are made: (1) a solution containing 0.25 wt % paclitaxel and 0.75 wt % polystyrene-polyisobutylene-polystyrene triblock copolymer (SIBS), prepared as described in United States Patent Application 20020107330 and U.S. Pat. No. 6,545,097 entitled "Drug delivery compositions and medical devices containing block copolymer"; (2) a solution containing 0.25 wt % paclitaxel and 0.75 wt % POSS copolymer prepared as described above; (3) a solution containing 0.25 wt % paclitaxel and 0.75 wt % poly(p-hydroxystyrene)-polyisobutylene-(p-hydroxystyrene) triblock copolymer prepared as described above (4) a solution containing 0.25 wt % paclitaxel and 0.5 wt % poly(p-hydroxystyrene)-polyisobutylene-(p-hydroxystyrene) triblock copolymer and 0.25 wt % SIBS, (5) a solution containing 0.25 wt % paclitaxel and 0.30 wt % poly(p-hydroxystyrene)-polyisobutylene-(p-hydroxystyrene) triblock copolymer and 0.45 wt % SIBS, (6) a solution containing 0.25 wt % paclitaxel and 0.1 wt % poly(p-hydroxystyrene)-polyisobutylene-(p-hydroxystyrene) triblock copolymer and 0.65 wt % SIBS, (7) a solution containing 0.25 wt % paclitaxel and 0.75 wt % poly(p-acetoxystyrene)-poly-isobutylene-(p-acetoxystyrene) triblock copolymer prepared as above, (8) a solution containing 0.088 wt % paclitaxel and 0.912 wt % SIBS, (9) a solution containing 0.25 wt % paclitaxel and 0.75 wt % poly(2-vinyl pyridine)-polyisobutylene-(2-vinyl pyridine) triblock copolymer prepared as above, (10) a solution containing 0.088 wt % paclitaxel and 0.912 wt % poly(2-vinyl pyridine)-polyisobutylene-(2-vinyl pyridine) triblock copolymer, (11) a solution containing 0.25 wt % paclitaxel and 0.75 wt % poly(cyclohexyl vinyl ether-co-vinyl alcohol)-polyisobutylene-poly(cyclohexyl vinyl ether-co-vinyl alcohol) triblock copolymer (with endblocks containing 25 mol % vinyl alcohol, prepared as above), (12) a solution containing 0.25 wt % paclitaxel and 0.75 wt % poly(cyclohexyl vinyl ether-co-vinyl alcohol)-polyisobutylene-poly(cyclohexyl vinyl ether-co-vinyl alcohol) triblock copolymer (with endblocks containing 50 mol % vinyl alcohol, prepared as above), (13) a solution containing 0.25 wt % paclitaxel and 0.75 wt % poly(cyclohexyl vinyl ether-co-vinyl alcohol)-polyisobutylene-poly(cyclohexyl vinyl ether-co-vinyl alcohol) triblock copolymer (with endblocks containing 75 mol % vinyl alcohol, prepared as above).

Each solution is then coated by spray coating as described, for example, in U.S. Patent Appln. Pub. No. 2003/0236514 to Schwarz. At least three stents are formed in this manner for each of the solutions.

Paclitaxel release is then measured as a function of time in PBS containing 0.5 wt % Tween® 20 (polyoxyethylene(20) sorbitan monolaurate) available from Sigma-Aldrich. The results, presented as the percentage of paclitaxel in the stent released as a function of time, are graphically illustrated in FIGS. 1-4.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising:
   (A) a polymeric region, said polymeric region comprising an elastomeric block copolymer that comprises a poly (p-acetoxystyrene)-polyisobutylene-(p-acetoxystyrene) triblock copolymer; and
   (B) a therapeutic agent disposed within or beneath said polymeric region;
wherein said medical device releases said therapeutic agent upon implantation or insertion into a subject and exhibits a sustained release profile with more than 50% of the total release of the therapeutic agent from the medical device occurring subsequent to 1 day of administration, said medical device being adapted for implantation or insertion into a subject's body.

2. The medical device of claim 1, wherein said therapeutic agent is disposed beneath said polymeric region.

3. The medical device of claim 1, wherein said therapeutic agent is disposed within said polymeric region.

4. The medical device of claim 1, wherein said polymer region further comprises an additional polymer in addition to said copolymer, and wherein said additional polymer is blended with said copolymer.

5. The medical device of claim 1, wherein said polymer region further comprises an additional polymer in addition to said copolymer, and wherein said additional polymer is attached to said copolymer.

6. The medical device of claim 1, wherein said polymeric region is disposed over a substrate.

7. The medical device of claim 1, wherein said medical device is selected from a guide wire, a balloon, a vena cava filter, a catheter, a stent, a stent graft, a vascular graft, a cerebral aneurysm filler coil, a myocardial plug, a heart valve, a vascular valve, and a tissue engineering scaffold.

8. The medical device of claim 1, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

* * * * *